United States Patent
Ashby et al.

(10) Patent No.: US 10,076,609 B2
(45) Date of Patent: Sep. 18, 2018

(54) SYRINGE HAVING A PISTON WITH EMBEDDED RFID CHIP

(71) Applicant: Parker-Hannifin Corporation, Cleveland, OH (US)

(72) Inventors: Dale M. Ashby, Solon, OH (US); Gino G. Banco, Lyndhurst, OH (US); Rene M. Beltran, Los Angeles, CA (US); Beth Keiper, San Bernardino, CA (US); Luis A. Hernandez, Baldwin Park, CA (US); Anthony Arispe, Riverside, CA (US); Tomas E. Carrillo, Torrance, CA (US)

(73) Assignee: Parker-Hannifin Corporation, Cleveland, OH (US)

( * ) Notice: Subject to any disclaimer, the term of this patent is extended or adjusted under 35 U.S.C. 154(b) by 624 days.

(21) Appl. No.: 14/422,108

(22) PCT Filed: Aug. 19, 2013

(86) PCT No.: PCT/US2013/055597
§ 371 (c)(1),
(2) Date: Feb. 17, 2015

(87) PCT Pub. No.: WO2014/028936
PCT Pub. Date: Feb. 20, 2014

(65) Prior Publication Data
US 2015/0217059 A1 Aug. 6, 2015

Related U.S. Application Data

(60) Provisional application No. 61/684,171, filed on Aug. 17, 2012.

(51) Int. Cl.
*B29C 45/14* (2006.01)
*A61M 5/315* (2006.01)
(Continued)

(52) U.S. Cl.
CPC .... *A61M 5/31513* (2013.01); *A61M 5/31511* (2013.01); *B29C 45/14065* (2013.01);
(Continued)

(58) Field of Classification Search
CPC .... B29C 2045/14852; B29C 45/14819; B29C 2045/14114; B29C 45/14065
See application file for complete search history.

(56) References Cited

U.S. PATENT DOCUMENTS 4,712,333 A * 12/1987 Lofton ................ B24B 31/14
241/184
5,317,663 A 5/1994 Beard et al.
(Continued)

FOREIGN PATENT DOCUMENTS

EP 0548612 A1 9/1993
WO 2005/099793 10/2005
(Continued)

OTHER PUBLICATIONS

International Preliminary Report on Patentability for corresponding Patent Application No. PCT/US2013/055597 dated Feb. 10, 2015.
(Continued)

*Primary Examiner* — Jill Lynne Heitbrink
(74) *Attorney, Agent, or Firm* — Renner, Otto, Boisselle & Sklar, LLP (57) ABSTRACT

Although injection molding includes extreme conditions, an RFID device may be over-molded by injection molding. A syringe includes a barrel having a first and second axial ends, the barrel defining a cavity therein; a plunger configured to be received in the cavity and define with the barrel a chamber for holding a fluid, the plunger being axially moveable within the barrel for increasing and decreasing the volume of the chamber thereby respectively forcing fluid into or out of the chamber; and a plunger seal, also known
(Continued)

as a "syringe stopper" for sealing between the plunger and the barrel, the plunger seal including an RFID device for identifying the syringe. The plunger seal may be made by injection molding.

13 Claims, 7 Drawing Sheets

(51) Int. Cl.
B29K 21/00 (2006.01)
B29L 31/00 (2006.01)

(52) U.S. Cl.
CPC ............ *A61M 2205/6009* (2013.01); *A61M 2205/6054* (2013.01); *A61M 2207/00* (2013.01); *B29C 2045/14114* (2013.01); *B29K 2021/003* (2013.01); *B29L 2031/7544* (2013.01)

(56) References Cited

U.S. PATENT DOCUMENTS

| | | |
|---|---|---|
| 6,441,741 B1 | 8/2002 | Yoakum |
| 6,778,089 B2 | 8/2004 | Yoakum |
| 7,158,034 B2 | 1/2007 | Corbett, Jr. |
| 8,282,013 B2 | 10/2012 | Stewart et al. |
| 2001/0034506 A1 | 10/2001 | Hirschman et al. |
| 2003/0030186 A1* | 2/2003 | Riiska ................ B29C 45/02 264/328.4 |
| 2006/0176180 A1* | 8/2006 | Freund ............ B29C 37/0032 340/572.8 |
| 2007/0219503 A1 | 9/2007 | Loop et al. |
| 2007/0246485 A1 | 10/2007 | Mathew |
| 2007/0257111 A1 | 11/2007 | Ortenzi |
| 2008/0094225 A1* | 4/2008 | Frankewich ......... A01K 27/009 340/573.1 |
| 2008/0191013 A1 | 8/2008 | Liberatore |
| 2008/0221549 A1 | 9/2008 | Cohen |
| 2009/0096629 A1 | 4/2009 | Sprowl et al. |
| 2011/0240747 A1 | 10/2011 | Stewart et al. |

FOREIGN PATENT DOCUMENTS

| | | |
|---|---|---|
| WO | 2007/101840 | 9/2007 |
| WO | 2010/133676 | 11/2010 |
| WO | 2011/032956 | 3/2011 |

OTHER PUBLICATIONS

Communication for related European Patent Application No. 13759046.9 dated Mar. 31, 2017.
International Search Report and Written Opinion for corresponding Patent Application No. PCT/2013/055597 dated Dec. 16, 2013.
International Written Opinion for corresponding Patent Application No. PCT/US2013/055597 dated Oct. 8, 2014.

* cited by examiner

SYRINGE HAVING A PISTON WITH EMBEDDED RFID CHIP

RELATED APPLICATIONS

This application is a national phase of International Application No. PCT/US2013/055597 filed on Aug. 19, 2013 and published in the English language, which claims the benefit of U.S. Provisional Application No. 61/684,171 filed Aug. 17, 2012, which is hereby incorporated herein by reference.

FIELD OF INVENTION

The present invention relates generally to the process of embedding RFID tags within polymers, and more particularly to the use of injection molding to overmold RFID-embedded polymeric components.

BACKGROUND

Radio-frequency identification (RFID) is the wireless use of radio-frequency electromagnetic fields to transfer data, often used to automatically identify and/or track objects via RFID devices attached to or otherwise associated with the objects. The RFID devices may contain electronically stored information. Some devices are powered by and read at short ranges (a few centimeters to a few meters) via magnetic fields (electromagnetic induction). These devices typically have no battery. Rather, they collect energy from the interrogating electromagnetic field. Other devices may use one or more local power sources such as a battery and then act as a transponder to emit radio waves. Battery powered tags may operate at up to hundreds of meters. RFID tags may be included in seals as described in U.S. Pat. No. 8,282,013, incorporated by reference herein in its entirety.

Injection molding often utilizes a ram or screw-type plunger to force melted polymer into a cavity of a mold (molds can include a single cavity or multiple cavities). The polymer solidifies into a shape conforming to the mold cavity. In multiple cavity molds, each cavity can be identical (to form the same parts) or can be unique (to form different geometries during a single cycle). Molds may be made of any suitable material, but are generally made from tool steels. Stainless steels and aluminum molds are suitable for certain applications. Although it wears faster, aluminum may be cost effective in low volume applications because mold fabrication costs and time can be considerably lower.

Pelletized raw thermoplastics, one type of polymer, may be fed through a hopper into a heated chamber with a reciprocating screw. The temperature increases and the Van der Waals forces that resist relative flow of individual chains in the material are weakened as a result of increased space between molecules. This reduces the material's viscosity, enabling the polymer to flow and be driven by the injection unit.

The reciprocating screw may deliver the raw material forward, mixing the polymer and reducing the required heating time by mechanically shearing the polymer and adding a significant amount of frictional heat. The material may be fed through a check valve and may collect at the front of the reciprocating screw into a volume known as a shot. The amount of material in a shot typically is sufficient to fill the mold cavity, compensate for shrinkage, and provide a cushion (approximately 10% of the total shot volume may remain in the chamber to prevent the screw from bottoming out) to transfer pressure from the screw to the mold cavity.

When enough material has gathered, the material may be forced at high pressure and velocity into the mold cavity. Injection times are usually quite quick, often well under 1 second. Packing pressure is applied to complete mold filling and compensate for thermal shrinkage. The packing pressure may be applied until the cavity entrance solidifies.

Next, the screw reciprocates and acquires material for the next cycle while the material within the mold cools, solidifying enough to be ejected. Cooling lines circulating fluid may reduce the required cooling time. Once cooled, the mold opens and an array of pins, sleeves, strippers, etc. may be driven forward to extract the molded element. Then, the mold closes and the process may be repeated.

SUMMARY OF INVENTION

Although injection molding includes extreme conditions, provided herein is a method of over-molding an RFID device by injection molding. Further provided is an RFID-embedded polymeric element, for example, an elastomeric plunger seal for a syringe.

According to one aspect of the invention, a syringe includes a barrel having a first and second axial ends, the barrel defining a cavity therein; a plunger configured to be received in the cavity and define with the barrel a chamber for holding a fluid, the plunger being axially moveable within the barrel for increasing and decreasing the volume of the chamber thereby respectively forcing fluid into or out of the chamber; and a plunger seal for sealing between the plunger and the barrel, the plunger seal including an RFID device for identifying the syringe.

Optionally, the plunger seal includes a generally cylindrical resilient body defining a central axis extending from a first axial end to a second axial end, and wherein the RFID device is embedded in the generally cylindrical resilient body.

Optionally, one of the first or second ends of the generally cylindrical body includes a frustoconical termination.

Optionally, the generally cylindrical resilient body includes a multi-ribbed sidewall.

Optionally, the generally cylindrical resilient body is monolithic.

Optionally, the RFID device is generally centered in the body relative to the central axis.

Optionally, the RFID device is a capsule.

Optionally, the RFID device is a flat circuit.

Optionally, the RFID device is a chip.

Optionally, the RFID device is a chip operatively coupled to a trailing antenna.

Optionally, the antenna is embedded in the plunger seal.

Optionally, the plunger seal is molded so as to embed the RFID device.

Optionally, the plunger seal is a monolithic structure.

Optionally, the plunger seal includes a first piece bonded to a second piece, the first and second piece defining a cavity therein, wherein the RFID device is positioned in the cavity of the plunger seal.

Optionally, the plunger seal comprises thermoplastic elastomer.

According to another aspect of the invention, a polymeric element includes a generally cylindrical resilient body defining a central axis extending from a first axial end to a second axial end; and an RFID device substantially enclosed by the resilient body.

Optionally, one of the first or second ends of the generally cylindrical body includes a frustoconical termination.

Optionally, the generally cylindrical resilient body includes a multi-ribbed sidewall.

Optionally, the generally cylindrical resilient body is monolithic.

Optionally, the RFID device is generally centered in the body relative to the central axis.

Optionally, the polymeric element is a plunger seal for a syringe.

Optionally, the RFID device is a capsule.

Optionally, the RFID device is a flat circuit.

Optionally, the RFID device is a chip.

Optionally, the RFID device is a chip coupled to a trailing antenna.

Optionally, the antenna is embedded in the polymeric element.

According to another aspect of the invention, a method of making a polymeric element includes attaching an RFID device to a holder of a mold core; inserting the mold core into a mold cavity; and injecting polymeric material into the mold to thereby form the polymeric element.

According to another aspect of the invention, a method of making an RFID-embedded polymeric element comprising the steps of attaching an RFID device to a holder of a mold core; inserting the mold core into a mold cavity; and injecting polymeric material into the mold cavity.

Optionally, the method includes curing the polymeric material.

Optionally, the method includes ejecting the polymeric element from the core with a stripper plate.

Optionally, the polymeric material is a thermoplastic elastomer.

Optionally, the polymeric element is an elastomeric seal.

Optionally, the polymeric element is a plunger seal for a syringe.

Optionally, the method includes inserting one or more cavity inserts into a mold to form the mold cavity.

Optionally attaching includes inserting the RFID device into a snap-fit holder.

Optionally, attaching includes adhesively attaching the RFID device to the holder.

Optionally, the method includes dissolving the holder.

The foregoing and other features of the invention are hereinafter described in greater detail with reference to the accompanying drawings.

DETAILED DESCRIPTION

Although injection molding includes extreme conditions, provided herein is a method of over-molding an RFID device by injection molding. Further provided is an RFID-embedded polymeric element, for example, an elastomeric plunger seal for a syringe. Although other RFID-embedded objects are possible (for example, O-ring seals, rigid-plastic components etc.) the example of the elastomeric plunger seal for a syringe will be used herein for brevity and clarity.

Figure 1:
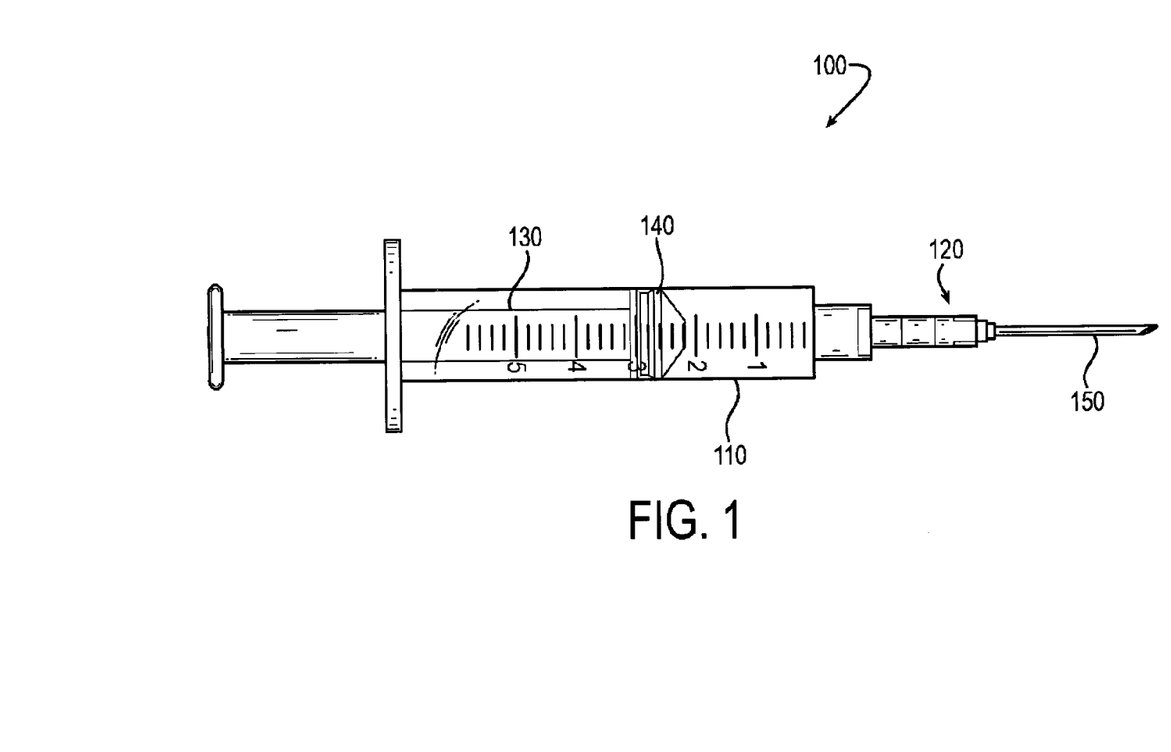
FIG. 1 shows an exemplary syringe.

Referring first to FIG. 1, a hydraulic or pneumatic syringe 100 is a simple pump including a barrel 110, an orifice 120, a plunger 130, and a plunger seal 140. Syringes may be used, for example to administer injections, draw blood, insert intravenous drugs into the bloodstream, apply compounds such as glue or lubricant, and measure liquids.

The barrel 110 is the main housing containing the fluid to be dispensed or drawn in, it is usually (though not necessarily) a cylindrical tube.

The plunger 130 is the component that creates positive or negative pressure within the barrel to dispense or draw in fluid. The plunger can be actuated, by, for example, being pulled and/or pushed along the inside of the barrel, allowing the syringe to take in and expel a liquid or gas through the orifice at the open end of the tube.

The plunger seal 140 may be an elastomeric seal or head that attaches to the plunger 130 to seal and contain the fluid within the barrel.

The open end of the syringe may be fitted with a hypodermic needle 150, a nozzle, or tubing to help direct the flow into and out of the barrel.

The plunger seal 140 may contain an embedded radio-frequency identification (RFID) device (not visible in FIG. 1). RFID is a means of wirelessly identifying and/or tracking an object using radio-frequency electromagnetic fields to transfer data from an RFID device attached to or otherwise associated with that object. RFID devices are classified by frequency into three categories: low frequency (LF), high frequency (HF), and ultra-high frequency (UHF). The devices are available in a variety of form factors (see FIG. 2) including capsules (used, for instance, as implantable means of pet/animal identification), flat RFID circuits with adhesive attached (used, for instance, to identify/track retail products), and electronic "chips" with trailing antennae (used for various longer range applications).

Embedding an RFID device within a plunger seal 140 allows identification and/or tracking of the syringe (or fluid therein) in a wireless manner that does not require any additional components or attachments to the syringe. The device is then "invisible" to the user, and does not interfere with the functionality of the syringe in any way. FIGS. 2A-4C show three exemplary embodiments of the RFID-embedded syringe plunger seal that may be manufactured by overmolding (for example, by injection molding). FIGS. 5A and 5B show another exemplary embodiment of a RFID-embedded syringe plunger seal in which the RFID device is disposed in a cavity formed between two or more separately formed portions that are bonded together to substantially surround the embedded RFID device.

Figure 2A:
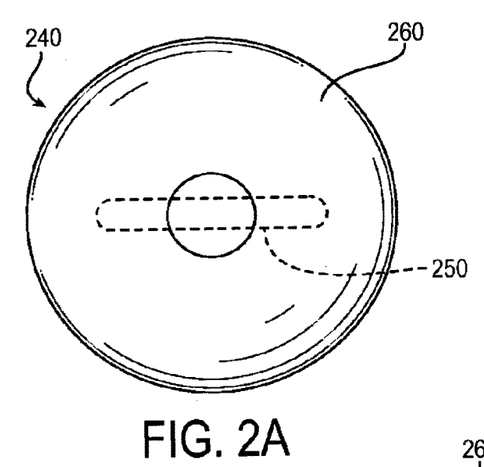
FIG. 2A shows a top view of an exemplary plunger seal.
Figure 2B:
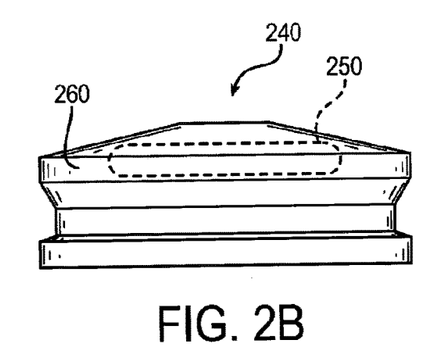
FIG. 2B shows a side view of an exemplary plunger seal.
Figure 2C:
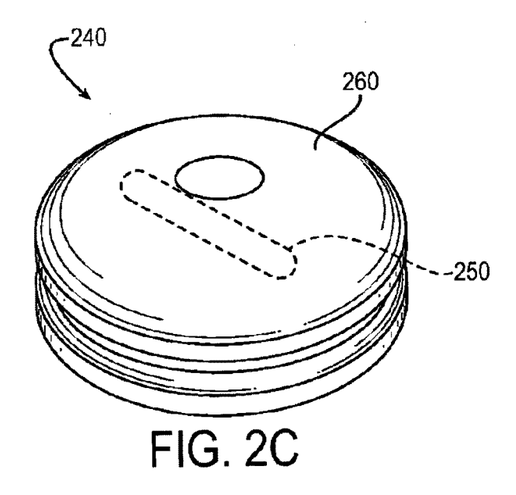
FIG. 2C shows a perspective view of an exemplary plunger seal.

FIGS. 2A-2C show an LF capsule type device 250 embedded within a plunger seal 240. In particular, the plunger seal 240 may be regarded as a polymeric element (in this case elastomeric), which includes an over-molded RFID device 250 substantially surrounded by a monolithic (as opposed to, for example, a multi-piece body bonded together as describe below) polymeric body 260. The plunger seal 240 is substantially the same as the above-referenced plunger seal 140, and consequently the same reference numerals but indexed by 100 are used to denote structures corresponding to similar structures in the plunger seal. In addition, the foregoing description of the plunger seal 140 is equally applicable to the plunger seal 240 except as otherwise noted. Moreover, it will be appreciated upon reading and understanding the specification that aspects of the plunger seals may be substituted for one another or used in conjunction with one another where applicable.

The body 260 may be generally cylindrical and resilient, and may define a central axis extending from a first axial end to a second axial end. The RFID device may be substantially enclosed by the resilient body.

One of the first or second ends of the generally cylindrical body may include a frustoconical termination, as illustrated, so as to compliment an internal shape of a syringe barrel. It is understood, however, that the end geometries may be made in any suitable shape, depending on the application.

As shown, the generally cylindrical resilient body may include a multi-ribbed sidewall to form redundant seals against an adjacent surface (for example, the inside of the syringe barrel).

Although not required in every application, exemplary embodiments generally center the RFID device in the body relative to the central axis.

Figure 3A:
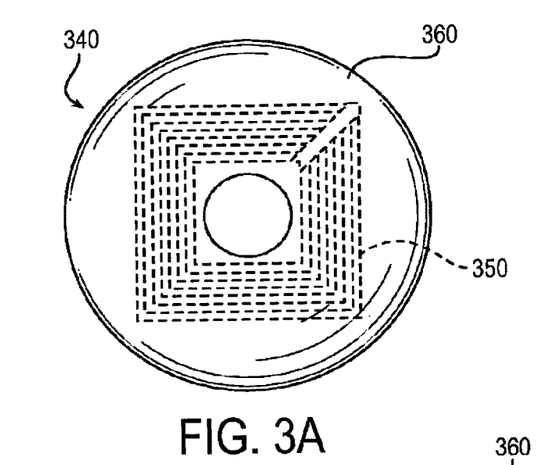
FIG. 3A shows a top view of an exemplary plunger seal.
Figure 3B:
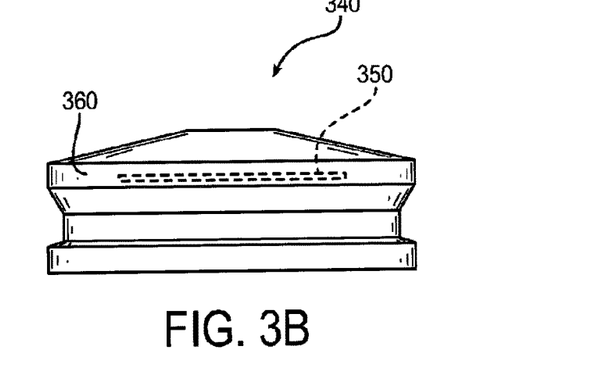
FIG. 3B shows a side view of an exemplary plunger seal.
Figure 3C:
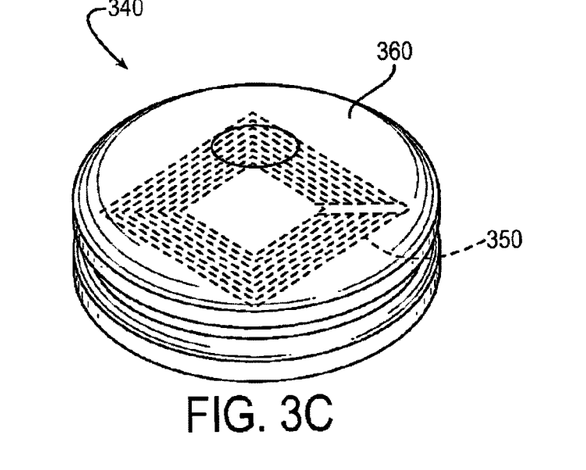
FIG. 3C shows a perspective view of an exemplary plunger seal.

FIGS. 3A-3C show an HF flat form factor device 350 embedded within a plunger seal 340. In particular, the plunger seal 340 may be regarded as a polymeric element (in this case elastomeric), which includes an over-molded RFID device 350 substantially surrounded by a monolithic polymeric body 360. The plunger seal 340 is substantially the same as the above-referenced plunger seals 140, 240 and consequently the same reference numerals but indexed by 100 are used to denote structures corresponding to similar structures in the plunger seal. In addition, the foregoing description of the plunger seals 140, 240 are equally applicable to the plunger seal 340 except as otherwise noted. Moreover, it will be appreciated upon reading and understanding the specification that aspects of the plunger seals may be substituted for one another or used in conjunction with one another where applicable.

Figure 4:
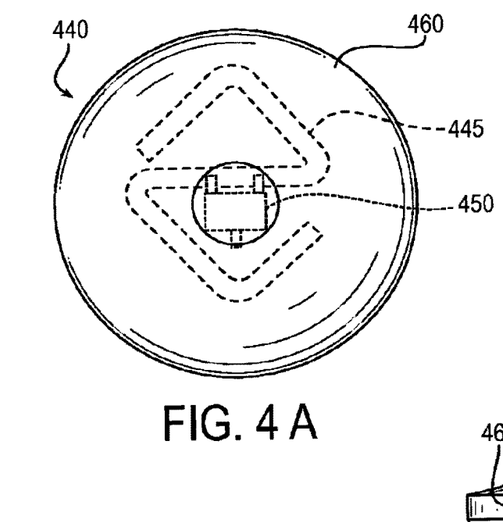
FIG. 4A shows a top view of an exemplary plunger seal.
FIG. 4B shows a side view of an exemplary plunger seal.
FIG. 4C shows a perspective view of an exemplary plunger seal.
Figure 4B:
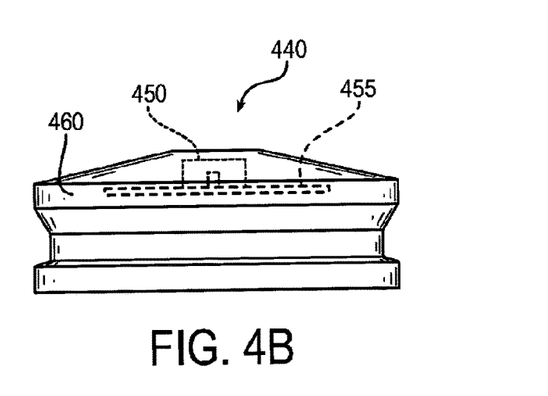
Figure 4C:
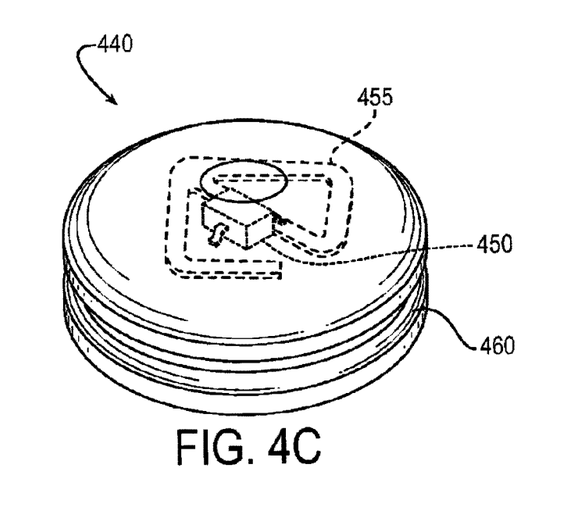
Figures 5A, 5B:
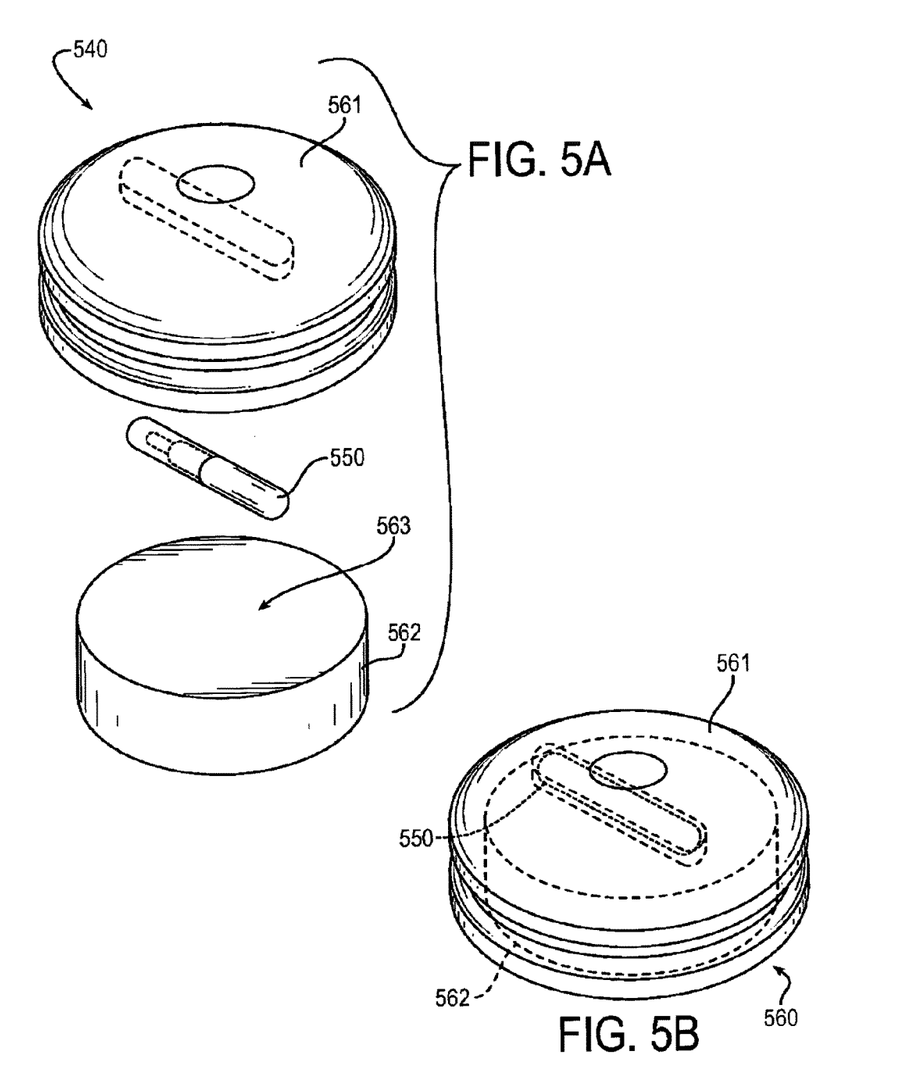
FIG. 5A shows an exploded view of an exemplary plunger seal.
FIG. 5B shows a perspective view of an exemplary plunger seal.

FIGS. 4A-4C show a UHF device 450 embedded within a plunger seal 440, including a possible orientation of the trailing antennae 455. In particular, the plunger seal 440 may be regarded as a polymeric element (in this case elastomeric), which includes an over-molded RFID device 450 substantially surrounded by a monolithic polymeric body 460. The plunger seal 440 is substantially the same as the above-referenced plunger seals 140, 240, 340 and consequently the same reference numerals but indexed by 100 are used to denote structures corresponding to similar structures in the plunger seal. In addition, the foregoing description of the plunger seals 140, 240, 340 are equally applicable to the plunger seal 440 except as otherwise noted. Moreover, it will be appreciated upon reading and understanding the specification that aspects of the plunger seals may be substituted for one another or used in conjunction with one another where applicable.

The RFID-embedded syringe plunger seal can utilize any of the various types of RFID devices if the seal can physically encapsulate the volume of the device.

The RFID devices can be embedded in various ways, including injection or compression molding, wherein the device is placed in a molding cavity and subsequently over-molded with elastomeric material. Molding would create embodiments such as those depicted in FIGS. 2A-4C, wherein the devices are completely over molded. These processes result in a single component with no (or very minimized) intended voids or cavities around the devices.

Another means of embedding the RFID device is to produce two or more pieces 561, 562 with a cavity 563 in one or more of the pieces, as shown in FIGS. 5A and 5B. The pieces are then bonded together in a secondary operation, creating the completed syringe seal 540. Creating the seal in two or more pieces is particularly well suited for an additive manufacturing process, such as stereo-lithography (SLA). FIGS. 5A and 5B show a multi-piece assembly incorporating an LF capsule type RFID device 550.

An advantage of exemplary polymeric elements is the ability to incorporate a means of wirelessly identifying the element (e.g., a syringe plunger seal) and thereby any assembly the element is a part of (e.g., a syringe system as a whole), without altering its form factor. Exemplary elements do not necessarily require a "stick-on" or otherwise attachable tag to be added to an existing system, which could be damaged or compromised via tampering. The RFID device is integrated within the system in an "invisible" manner such that it cannot be seen, or tampered with, and does not interfere with the functionality consistent with a corresponding device that does not have the RFID device.

The body of exemplary seals may be conventionally molded, extruded and cut, or otherwise formed of an elastomeric material which specifically may be selected for low or high temperature performance, flexibility, or otherwise for compatibility with the fluid being handled. Suitable materials, which may be filled, for example, with glass or carbon black, or which may be unfilled, include natural rubbers such as Hevea and thermoplastic, i.e., melt-processible, or thermosetting, i.e., vulcanizable, synthetic rubbers such as: fluoro- or perfluoroelastomers, chlorosulfonate, polybutadiene, butyl, neoprene, nitrile, polyisoprene, buna-N, copolymer rubbers such as ethylene-propylene (EPR), ethylene-propylene-diene monomer (EPDM), acrylonitrile-butadiene (NBR or HNBR) and styrene-butadiene (SBR), and blends such as ethylene or propylene-EPDM, EPR, or NBR. The term "synthetic rubbers" also should be understood to encompass materials which alternatively may be classified broadly as thermoplastic or thermosetting elastomers such as polyurethanes, silicones, fluorosilicones, styrene-isoprene-styrene (SIS), and styrene-butadiene-styrene (SBS), as well as other polymers which exhibit rubber-like properties such as plasticized nylons, polyolefins, polyesters, ethylene vinyl acetates, fluoropolymers, and polyvinyl chloride. As used herein, the term "elastomeric" is ascribed its conventional meaning of exhibiting rubber-like properties of compliancy, resiliency or compression deflection, low compression set, flexibility, and an ability to recover after deformation, i.e., stress relaxation.

However, in preferred embodiments, and as further described below, exemplary seals may be preferably injection molded of thermoplastic elastomers.

One or more RFID devices (exemplary seals preferably include one) may be embedded in exemplary polymeric elements. The RFID device(s) may be provided as a passive tag or similar device including an onboard chip which may function both as a radio receiver and transmitter, as well as an electronic data storage medium, and tuned conductor, which acts as an antenna. As it may be so provided, such transponder requires neither an internal power source which would need replacement, nor an external power source or other component which would require hardwire or other connections extending out of the body that could interfere with the function of the element (for example, by interfering with the sealing ability of a seal).

Following formation of an RFID-embedded polymeric element, the RFID device may be encoded or otherwise programmed with information specific to the element such as its part, serial, batch and/or lot number, material code, dimensions, date of manufacture, sale, installation, and/or expiration date. The RFID device also may be programmed with a unique identifier or code which may be cross-referenced to an electronic database or other compilation of such information. With the RFID device so programmed, it may be queried with an associated reader (not shown) which likewise may be programmed to store and interpret the data received from the RFID device. Such data may be used by a manufacturer, stocking distributor, and/or end user before or after the element is put into service, such as for assembly, inventory control, and/or maintenance purposes. For example, an element may be identified using the reader without the need for supporting documentation such as a label or packaging. The element also may be linked via the reader to application, service, or other information provided by the manufacturer.

Figure 6:
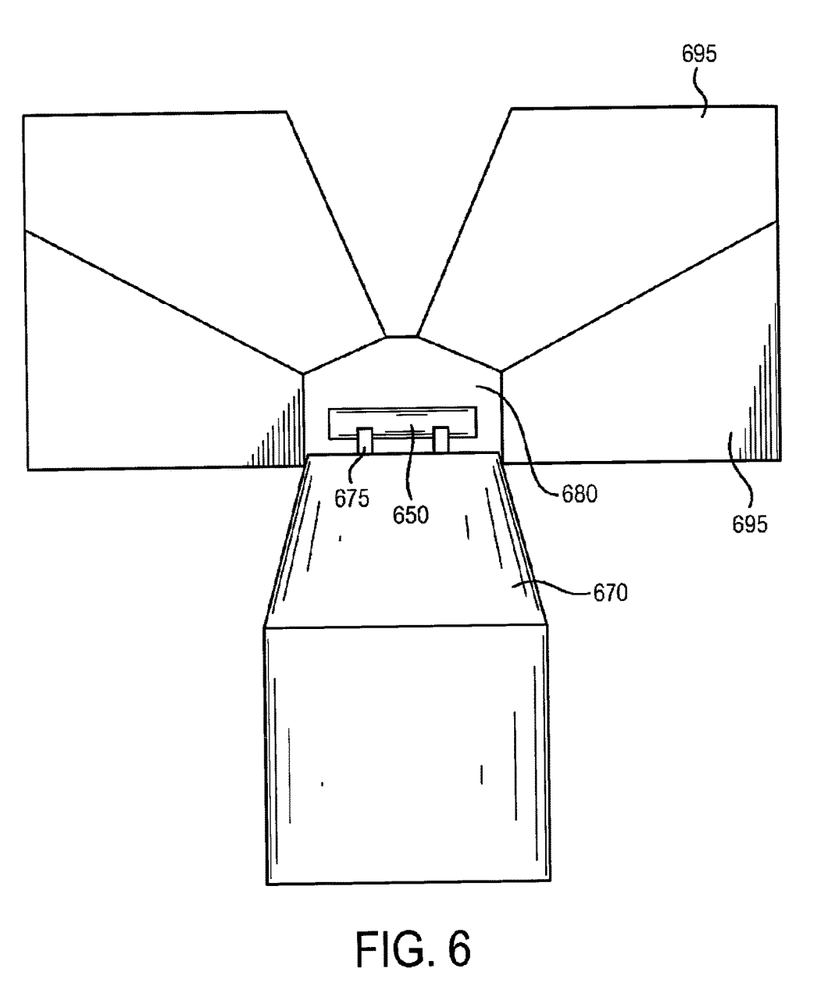
FIG. 6 shows a schematic partial cross-sectional view of an exemplary mold.
Figure 7:
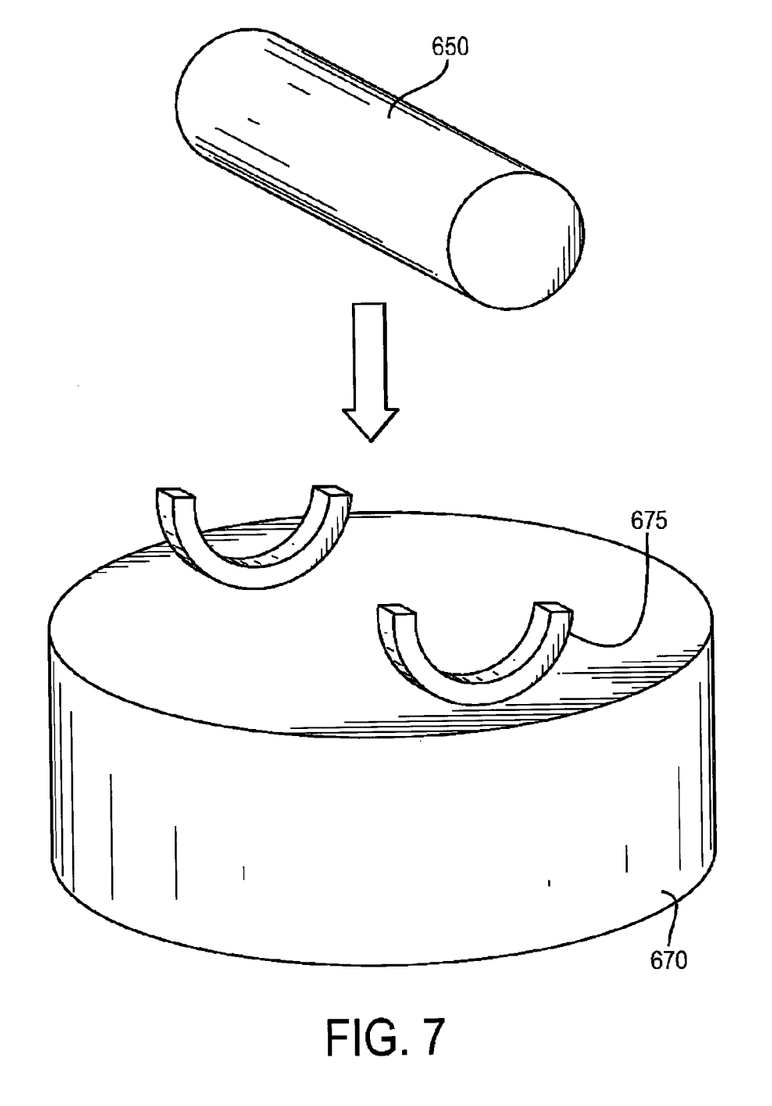
FIG. 7 shows a partial schematic view of an exemplary mold.

Turning now to FIGS. 6 and 7, a method of making an RFID-embedded polymeric element (for example, an exemplary elastomeric plunger seal) may include the steps of 1) attaching an RFID device 650 to a holder 675 of a mold core 670; 2) inserting the mold core 670 into a mold cavity 680; and 3) injecting polymeric material into the mold cavity 680.

After injecting the polymeric material, the polymeric material may be allowed to cure.

After curing, the cured polymeric element may be ejected from the core (for example, by a stripper plate).

Prior to injection, one or more cavity inserts 695 may be inserted into the mold 690 to form the mold cavity 680.

Attaching the RFID device to the holder may include inserting the RFID device into a snap-fit holder as shown in FIG. 7. In particular, the holder may include a slot configured to conform generally to the shape of the RFID device and a sub-insert with two half circle-like features to retain, with, for example, a snap-fit, (as shown in FIG. 7) the RFID device in place during the molding process. Inserting the RFID device (especially with a capsule type device) into the slot of the core by may be done by hand (or may be automated) and should be inserted with a very slight force (to avoid damaging the device) to ensure the RFID device is properly secured in the holder of the core.

Alternatively or additionally, the RFID device may be attached to a holder adhesively. RFID Tags may be placed onto a thin adhesive film which will be placed over the core. The adhesive on the film may maintain the RFID devices in place during the mold injection process, and may assist in positioning the devices in the cavity. The Tags may be installed on the film manually and then a robotic arm may pick up the film and place it over the mold (i.e., core). The film may be designed to dissolve prior ejection of parts to avoid waste and any cross contamination.

In exemplary embodiments, as described above, the polymeric material is a thermoplastic elastomer.

The mold configuration should allow a wall thickness between the RFID device and outer skin of the polymeric element of at least 0.050 of an inch to ensure a full coverage of the RFID device.

Other applications where a polymeric (e.g., an elastomeric) material is employed with enough volume to accommodate an RFID device may also use this method. This can include medical devices or systems such as vials, containers, catheters, tubing sets, bandages, tags, bed mats, wraps, gels, etc.; appliance housings; toys; etc.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of making an elastomeric plunger seal for a syringe, the syringe comprising: a cylindrical resilient body defining a central axis extending from a first axial end to a second axial end and a resilient circumferential sidewall extending along the central axis and configured to seal against an inside wall of the syringe; and an RFID device within the resilient body, the method comprising the steps of:
   attaching an RFID device to a holder of a mold core;
   inserting the mold core into a mold cavity; and
   injecting polymeric material into the mold to thereby form the elastomeric plunger seal, the RFID device provided within the cylindrical resilient body between the first and second axial ends and encompassed by the resilient circumferential sidewall such that the RFID device is unexposed at a face of the resilient circumferential sidewall.

2. The method of claim 1, further comprising:
   curing the polymeric material.

3. The method of claim 1, further comprising:
   ejecting the polymeric element from the core with a stripper plate.

4. The method of claim 1, wherein the polymeric material is a thermoplastic elastomer.

5. The method of claim 1, further comprising:
   inserting one or more cavity inserts into a mold to form the mold cavity.

6. The method of claim 1, wherein attaching includes inserting the RFID device into a snap-fit holder.

7. The method of claim 1, wherein attaching includes adhesively attaching the RFID device to the holder.

8. The method of claim 1, further comprising:
   dissolving the holder.

9. The method of claim 1, wherein one of the first or second ends of the generally cylindrical body includes a frustoconical termination.

10. The method of claim 1, wherein the generally cylindrical resilient body includes a ribbed sidewall having one or more ribs.

11. The method of claim 10, wherein the RFID device does not form a part of the one or more ribs.

12. The method of claim 11, wherein the RFID device is provided between the first and second axial ends such that the RFID device is unexposed at a face of the first axial end and at the second axial end.

13. The method of claim 1, wherein the RFID device is provided between the first and second axial ends such that the RFID device is unexposed at a face of the first axial end and at the second axial end.

* * * * *